(12) United States Patent
Engle et al.

(10) Patent No.: US 8,261,618 B2
(45) Date of Patent: Sep. 11, 2012

(54) DEVICE FOR MEASURING PROPERTIES OF WORKING FLUIDS

(75) Inventors: Brian Allen Engle, Armada, MI (US); Matthew Ingco, Palo Alto, CA (US); Chris Wagner, San Jose, CA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/951,330

(22) Filed: Nov. 22, 2010

(65) Prior Publication Data

US 2012/0125115 A1     May 24, 2012

(51) Int. Cl.
*G01L 9/06*     (2006.01)

(52) U.S. Cl. ........................................... 73/727; 73/754
(58) Field of Classification Search ............. 73/700–756
See application file for complete search history.

(56) References Cited

U.S. PATENT DOCUMENTS

| | | | |
|---|---|---|---|
| 4,310,357 A | 1/1982 | Matsuura et al. | |
| 4,743,302 A | 5/1988 | Dumesnil et al. | |
| 5,334,558 A | 8/1994 | Dietz et al. | |
| 5,663,109 A | 9/1997 | Dietz et al. | |
| 7,053,493 B2 * | 5/2006 | Kanda et al. | 257/783 |
| 7,585,798 B2 | 9/2009 | Yoshida et al. | |
| 2002/0158550 A1 * | 10/2002 | Yamaguchi | 310/324 |
| 2003/0098771 A1 * | 5/2003 | Padmanabhan et al. | 338/25 |
| 2004/0043479 A1 * | 3/2004 | Briscoe et al. | 435/288.5 |
| 2005/0218757 A1 * | 10/2005 | Yamaguchi et al. | 310/365 |
| 2006/0108896 A1 * | 5/2006 | Nanataki et al. | 310/324 |
| 2006/0108897 A1 * | 5/2006 | Nanataki et al. | 310/324 |
| 2009/0291822 A1 | 11/2009 | Shyu et al. | |

FOREIGN PATENT DOCUMENTS

JP     08153821 A   *   6/1996
JP     2004071698 A   *   3/2004

* cited by examiner

*Primary Examiner* — Andre Allen
(74) *Attorney, Agent, or Firm* — Global Patent Operation; Mark A. Conklin

(57) ABSTRACT

There are provided embodiments of a sensing device that comprise a sensing element, a substrate, and a bonding element, each being selected for environments that utilize caustic working fluids such as automotive fuel. Material for use as the bonding element can form molecular bonds with ceramics and glass. In one embodiment, the sensing device comprises a receptacle or cavity, in which are located the sensing element and the bonding element. This configuration facilitates the formation of bonds between the bonding element and each of the sensing element and a peripheral wall of the cavity. Such bonds are configured in a tensile bonding area and a shear bonding area, the combination of which is useful to secure the sensing element in the cavity. The sensing device can further comprise a seal such as an o-ring disposed in annular relation to the substrate to seal the sensing device to a peripheral device such as a fluid fitting, which may be found in a fuel system of an automobile.

20 Claims, 5 Drawing Sheets

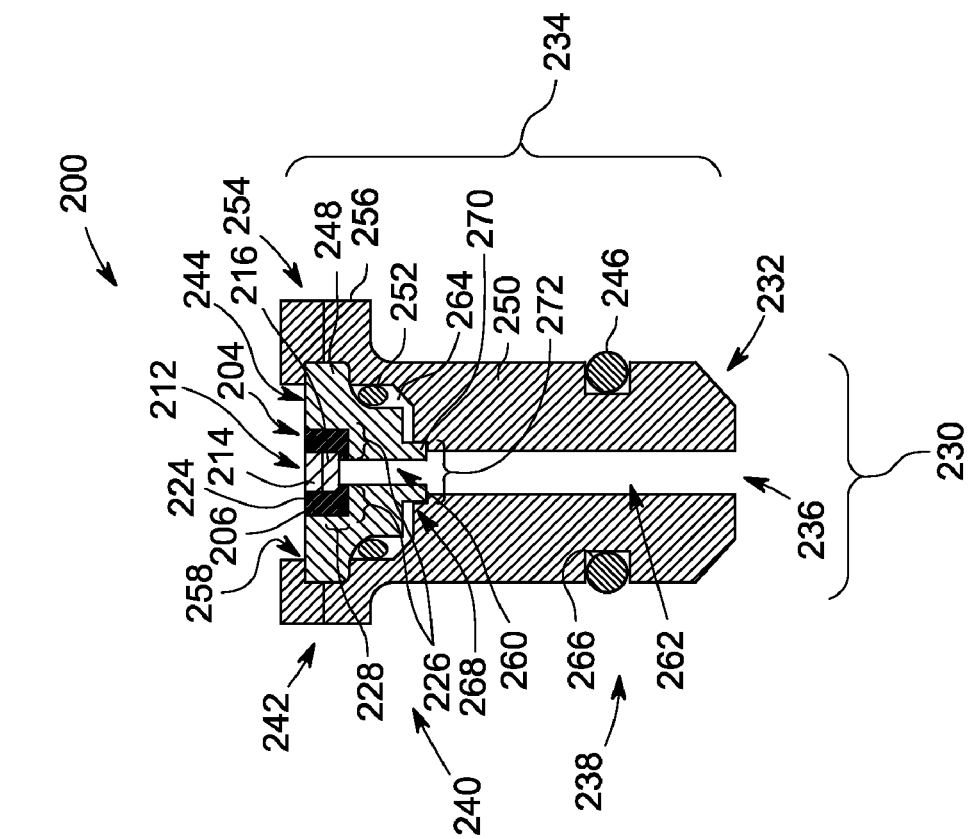
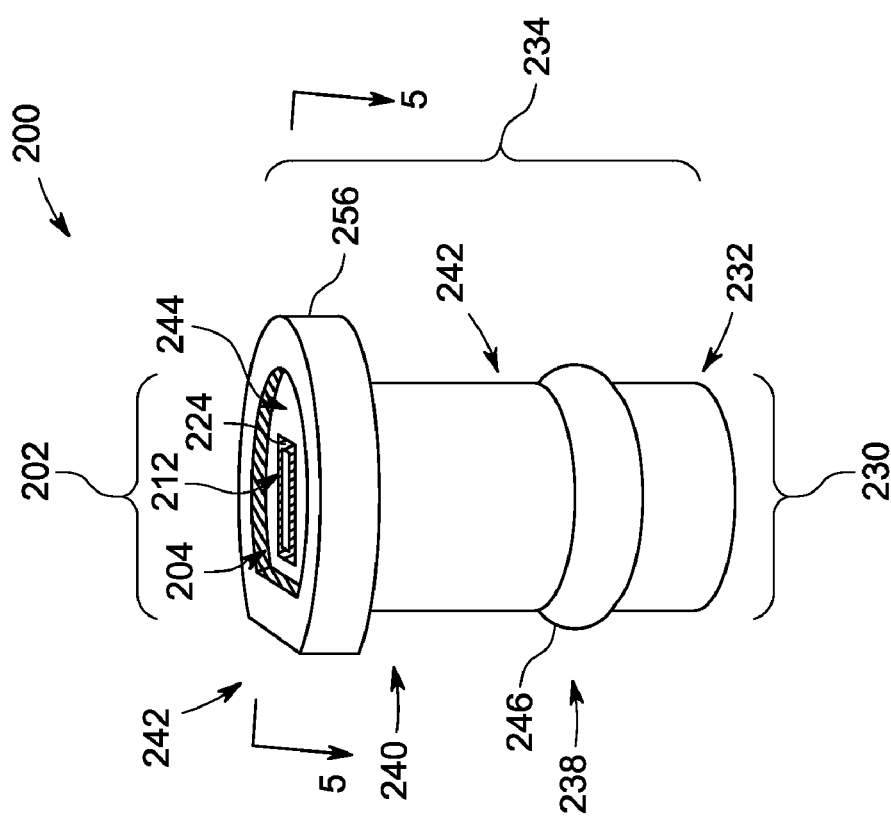
FIG. 5
FIG. 4

DEVICE FOR MEASURING PROPERTIES OF WORKING FLUIDS

BACKGROUND OF THE INVENTION

The subject matter disclosed herein relates generally to sensors, and more particularly, to embodiments of a sensing device that are configured to measure properties of caustic working fluids such as fuel, coolant, oils, and hydraulic fluids used in an automotive vehicle.

Sensor assemblies can comprise threaded metal or plastic that can form discrete threaded housings or threaded interfaces, which can be incorporated into other functional components such as fluid fittings. These sensor assemblies may incorporate sensing elements that are responsive to one or more properties of a working fluid (e.g., fuel). Temperature sensors, pressure sensors, flow sensors, and the like are all suitable sensing elements that can be incorporated as part of the sensor assembly. Certain applications may require that these sensor assemblies, as well as or in addition to the fluid fittings in which the sensor assembly is incorporated, are constructed so that each can withstand the physical and the chemical characteristics particular to the working fluid and/or the environment that utilizes the working fluid. Exemplary environments can include systems such as fuel, coolant, lubrication, hydraulic, and brake systems, all of which can be found in automobiles.

While some sensors are compatible with fittings for use in these environments, such as sensors that can monitor properties of the working fluids in automotive systems, few of these sensors incorporate semiconductor devices such as semiconductor-based die, ceramic-based die, or other die with similar capacitive properties. One reason for this is the inadequate construction of the sensor. For example, circuitry for many silicon-based die (e.g., piezo-resistive pressure sensor die) are manufactured on silicon wafers. These wafers may require a supportive structure that is bonded to the backside of the wafer. This structure can be constructed of materials (e.g., glass) that have a coefficient of thermal expansion ("CTE") that is similar to the CTE of the silicon wafer. Further processing of the wafer can result in generally cubic sensing packages that comprise the silicon/glass assembly. To form the sensor, these cubic sensing packages can be attached to a secondary substrate such as polymeric thermoplastics, which are generally selected because these materials are resistant to the chemical properties of the working fluid.

An epoxy is typically used to bond the glass portion of the wafer/glass assembly to the substrate. However, epoxies tend to act on the surface microstructure as between the glass and the plastic substrate. This action forms a mechanical bond, which can degrade when exposed to the working fluid. For example, the properties of the mechanical bond can change over time as the hydrocarbons in the epoxy cross-link and change their material characteristics in response to temperature and chemical attack. Moreover, because the epoxy materials that are used to bond the glass and plastic together have a CTE from about 20 ppm/° C. to about 100 ppm/° C., these epoxies expand and contract at a rate that is greater than either the glass or silicon of the sensing package. This rate can cause cyclic shear fatigue, thus making epoxies poor bonding materials for environments that exhibit large deviations in temperatures and/or high pressures.

There are fittings that are constructed to overcome some of these issues. Such sensors may incorporate ceramic capacitive circuits that are printed on stainless steel foil. Fittings that utilize this configuration, however, often comprise large stainless steel housings and connective mechanisms (e.g., threaded connectors, brazed and welded joints) for securing the housing to the fluid-carrying pipe. This construction causes the resulting fitting to be large and bulky, characteristics which are problematic and ill-suited for many automotive systems. For example, space constraints in the automobile structure can limit the packaging size so that large fittings may necessitate costly design changes to the components and their layout within the vehicle structure.

Therefore, it would be advantageous to provide a sensor that can withstand caustic working fluids, but that is designed and manufactured for robust and varied applications. It would be advantageous, for example, to provide a sensor for measuring properties of caustic working fluids with improved accuracy and reliability, but that is constructed in a manner compatible with fittings that meet cost, size, and other design constraints of the automotive industry.

BRIEF DESCRIPTION OF THE INVENTION

In one embodiment, a sensing device comprises a sensing region, a sensing element disposed in the sensing region, and a bonding element. In one example, the bonding element forms a first bonding area that comprises a molecular bond between the bonding element and a side of the sensing element. In another example, the bonding element has a coefficient of thermal expansion that is less than about 10 ppm/° C.

In another embodiment, a device for measuring a property of a working fluid. The device comprises a substrate with a cavity having a peripheral wall and a discrete sensing device having a bonded portion disposed in the cavity. The device also comprises a bonding element disposed between the bonded portion and the peripheral wall, the bonding element forming a molecular bond with the bonded portion and the peripheral wall. In one example, the bonding element has a coefficient of thermal expansion that is less than about 10 ppm/° C.

BRIEF DESCRIPTION OF THE DRAWINGS

So that the manner in which the features of the invention can be understood in detail, a detailed description of which can be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the principles of certain embodiments of invention.

Thus, for further understanding of the invention, references can be made to the following detailed description, read in connection with the drawings in which:

FIG. 4 is a perspective, side view of a sensing device that is made in yet another exemplary embodiment of the invention.

FIG. 5 is a side, cross-section, assembly view of the sensing device of FIG. 4.

DETAILED DESCRIPTION OF THE INVENTION

Broadly stated, there is described below embodiments of a sensing device for measuring properties of a fluid. These sensing devices incorporate concepts and features that can improve the quality, reliability, and compatibility of the sensing device as these sensing devices are implemented in systems with working fluids such as automotive fuel, hydraulic fluids, lubricants, coolant, refrigerants, and similar caustic materials. Among the concepts disclosed below, sensing devices of the present disclosure are configured to reduce degradation using a bonding element to adjoin the device to the substrate. In one embodiment, the bonding element, the device, and the substrate are configured to take advantage of both the shear and tensile properties of the material of the bonding element.

More particular to one or more embodiments discussed below, the inventors have identified combinations of structure and materials (and related manufacturing processes) that can be used to improve the effectiveness of these sensing devices. Materials are used that promote bonding at the molecular level, rather than utilizing mechanical bonding at the microstructure level discussed above. Moreover, in one embodiment, the sensing device is constructed to take advantage of the shear strength of the molecular bonds. Sensing devices that utilize these concepts can maintain the pressure of the working fluids such as in the fitting, while also being configured to measure certain properties of the working fluid such as temperature, pressure, flow rate, material properties, and the like. These features are effective to provide sensing devices that are compact enough to be implemented as part of fluid fittings, which are configured to be compatible with the working fluids as well as with the extremely confined package space such as within the valve body of a transmission.

Figure 1:
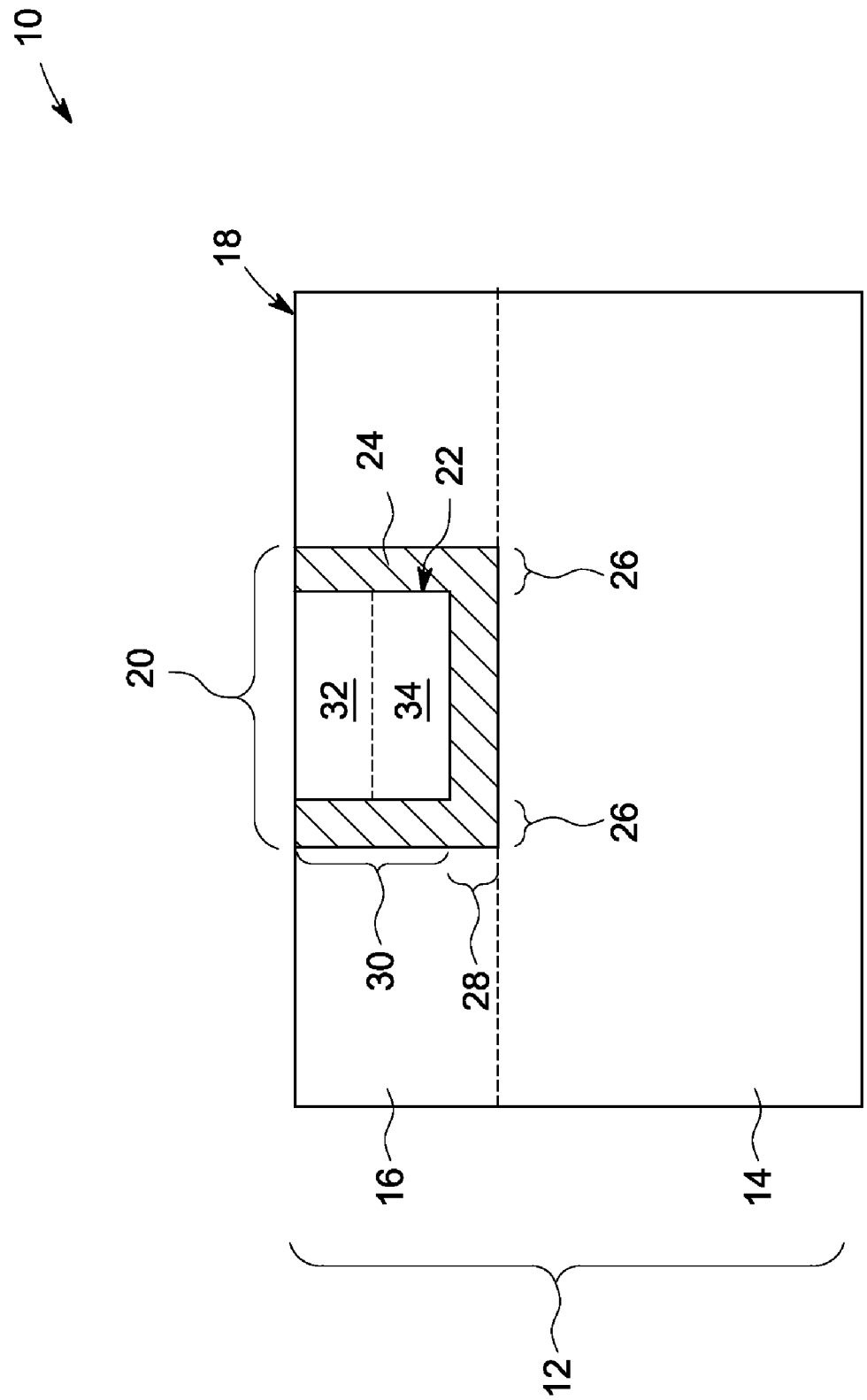
FIG. 1 is functional block diagram that illustrates a sensing device in an exemplary embodiment of the invention.

To illustrate some of these concepts reference can be had to the functional block diagram of FIG. 1, which illustrates at a relatively high level one exemplary embodiment of a sensing device 10. The sensing device 10 can have a multi-layered structure 12 that can comprise a lower or first region 14 and an upper or second region 16. Together the first region 14 and the second region 16 can form a substrate 18, which can have a sensing region 20 in which is disposed a sensing element 22. A bonding element 24 can be positioned to bond the sensing element 22 to one or more of the first region 14 and the second region 16. In one example, the bonding element 24 can form a shear or first bonding area 26 and a tensile or second bonding area 28. The sensing element 22 can further comprise a device level structure 30, and in the construction shown in FIG. 1 the device level structure 30 can comprise a primary layer 32 and a supporting layer 34 (collectively referred to hereinafter as "the sensing device layers"). In one example, the primary layer 32 and the supporting layer 34 are bonded together using anodic bonding, a concept recognized in the art and thus not discussed in detail herein.

The sensing element 22 can be a type of discrete sensing device constructed at least in part as a silicon die or similar semiconductor-based device circuit. This circuit can have functionality designed for measuring one or more properties of the working fluid. In addition to the generally recognized materials for use with semiconductor devices, the sensing device layers of the present application can also comprise other materials including, but not limited to, ceramics, glass, semiconductor materials such as silicon carbide and gallium arsenide, as well as other materials that do not substantially degrade when brought in contact with the working fluid.

In one embodiment, the materials for one or more of the substrate 18, including the first region 14 and the second region 16, the sensing element 22, and the bonding element 24 are selected to reduce the differences in the thermal expansion and contraction as between the various materials, layers, and components of the sensing device 10. The inventors have discovered that internal and external forces (e.g., stress and strain) on the sensing element 22 are reduced by selecting materials that are both compatible with the working fluid and also have substantially consistent thermal properties as measured by, e.g, the coefficient of thermal expansion ("CTE") of the materials. This is particularly beneficial because in the example of a silicon die stress relief caused by differential rates of thermal expansion and/or contraction can deteriorate performance of the sensing device 10 such as by reducing the accuracy of the silicon die, while generally making the sensing device 10 (and any corresponding device in which the sensing device 10 is implemented) ultimately susceptible to leaks and other catastrophic failures.

The properties of materials that can be used in one non-limiting example of the sensing device 10 are shown in Table 1 below,

TABLE 1

| PROPERTIES | Substrate 18 | Bonding Element 24 | Primary Layer 32 | Supporting Layer 34 |
|---|---|---|---|---|
| Young's modulus, Gpa | 300 | 62.08 | 112.4 | 62.75 |
| Poisson's ratio | 0.22 | 0.25 | 0.28 | 0.2 |
| CTE | 6.4 | 7.7 | 2.49 | 3.25 |
| Density, g/cc | 3.8 | 7.6 | 2.329 | 2.23 |
| Thermal Conductivity, W/m-K | 25 | NA | 124 | NA |
| Flexural Strength, Mpa | 320 | NA | NA | NA |

The substrate 18 can be formed monolithically, such as wherein the first region 14 and the second region 16 (collectively, "the substrate regions") are integrally manufactured from the same material. In one example, the material can be etched to prepare the sensing region 20 for receiving the sensing element 22. Each of the sensing regions in other embodiments can be formed separately of the same or different material and construction. Although not illustrated in FIG. 1, when separately manufactured, bonding material or layers can be incorporated into the sensing device 10 to secure together the substrate regions. In one example, this bonding material can be the same material as the bonding element 24.

Figure 3:
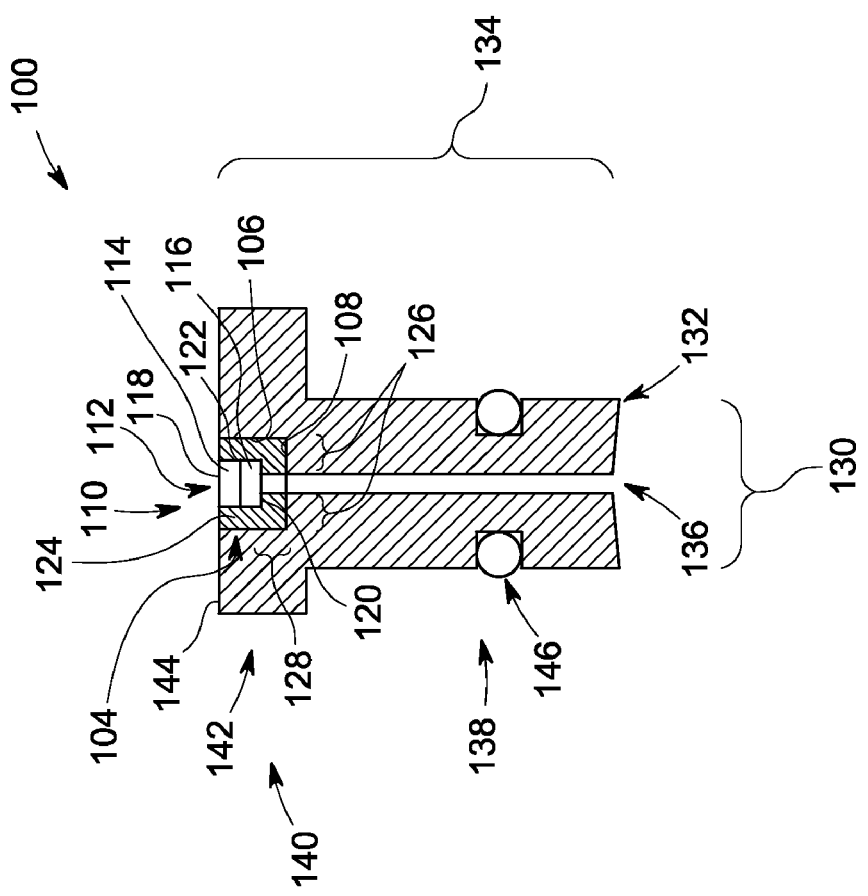
FIG. 3 is a side, cross-section, assembly view of the sensing device of FIG. 2.
Figure 2:
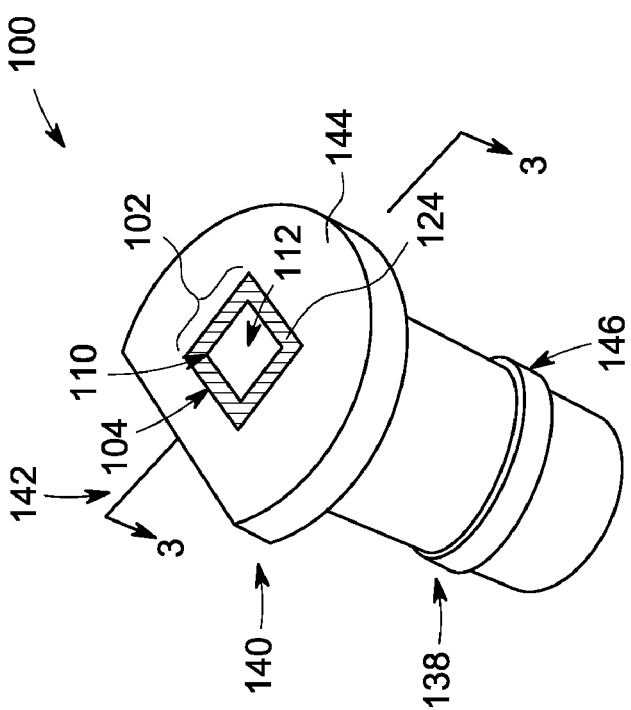
FIG. 2 is a perspective, side view of a sensing device in another exemplary embodiment of the invention.

Turning next to FIGS. 2 and 3, one or more of the concepts identified above in connection with the sensing device 10 (FIG. 1) are implemented in another exemplary embodiment of a sensing device 100. The sensing device 100 can comprise a sensing region 102 in which is found a receptacle or cavity 104 with a peripheral cavity wall 106 and a bottom cavity surface 108. The cavity 104 can be sized and configured to receive at least a portion of a sensing element 110 such as a discrete sensing device 112 with a primary layer 114 and a supporting layer 116. In one example, the discrete sensing device 112 can include a top 118, a bottom 120, and sides 122. The sensing device 100 can also comprise a bonding element 124, which is comprised of a material that is used to secure the discrete sensing device 112 in the cavity 104. In one example, the bonding element 124 can form a shear or first bonding area 126, such as between the peripheral cavity wall 106 and the sides 122 of the discrete sensing device 112, and a tensile or second bonding area 128 between the bottom cavity surface 108 and the bottom 120 of the discrete sensing device 112.

The sensing device 100 can also comprise a substrate 130 in the form of a housing 132. The housing 132 can have an elongated body 134 with a fluid passage 136 extending therethrough. The elongated body 134 can be configured with a lower body portion 138 and an upper body portion 140, which in one construction can incorporate and/or form the cavity 104. The upper body portion 140 can also comprise an indexing feature 142 such as a tab or a flat that can prevent movement (e.g., rotation) of the sensing device 100 when mounted in, e.g., the fluid fitting. Further retention of the sensing device 100 is facilitated by way of a vertical restraining surface 144, which can be configured to engage one or more complementary features on the fluid fitting. In one embodiment, the sensing device 100 can also comprise a seal 146 such as the axial O-ring seal depicted in FIGS. 2 and 3, which in the present example extends substantially annularly around the periphery of the elongated body 134.

As depicted in FIGS. 2 and 3, in one embodiment the bonding element 124 is disposed in the cavity 104 such as by deposition or other manufacturing process (e.g., screen printing). Depositing the bonding element 124 in this manner places the bonding element 124 adjacent one or more of the sides 122 of the discrete sensing device 112 and the peripheral cavity wall 106. In one embodiment, this placement facilitates formation of the first bonding area 126, wherein molecular bonds are formed between the bonding element 124 and each of the sides 122 and the peripheral cavity wall 106. Other embodiments are likewise configured so that the material of the bonding element 124 is found subjacent the bottom 120 of the discrete sensing device 112. This subjacent material is provided to facilitate formation of the second bonding area 128 in which molecular bonds are formed between the bonding element 124 and each of the bottom 120 of the discrete sensing device 112 and the bottom cavity surface 108 of the cavity 104. In one embodiment, the subjacent material may be omitted, however, in lieu of construction of the sensing device 100 in which only the first bonding area 126 is present. An exemplary representation of the second bonding area 128 is best illustrated in FIG. 3.

Formation of the first bonding area 126 can comprise varying portions of the peripheral cavity wall 106 and the sides 122 of the discrete sensing device 112. As depicted in FIGS. 2 and 3, the cavity 104 can have sufficient depth so that most if not all of the discrete sensing device 112 is seated inside of the cavity 104. The bonding element 124 can be used to fill in the areas about the discrete sensing device 112, forming a bonded portion that includes portions of the sides 122 and portions of the peripheral cavity wall 106. In one non-limiting example, the bonded portion incorporates at least 50% of the sides 122 of the discrete sensing device 112. In another example, the bonded portion incorporates from about 25% to about 75% of the sides 122 of the discrete sensing device 112. In yet another example, the bonded portion is constructed so that the shear strength of the bonds in and around the first bonding area 126 can withstand at least the pressure of the working fluid that impinges on the discrete sensing device 112. It is further contemplated that embodiments of the sensing device 100 can be configured so that the bonded portion covers various portions of the sides 122. In one example, the bonded portion may include a first percentage of a first side and a second percentage of a second side. Constructions of the sensing device 100 can be configured wherein the first percentage is different that the second percentage, and also where the first percentage is the same or similar to the second percentage.

The primary layer 114 and the supporting layer 116 can comprise, respectively, silicon and glass (e.g., PYREX). In other examples, the supporting layer 116 can comprise one or more materials with properties that are similar to silicon and/or the semiconductor materials used in the primary layer 114 or other portion of the discrete sensing device 112. The configuration of the primary layer 114 and the supporting layer 116 are non-limiting, but rather are provided to exemplify one type of device structure for the discrete sensing device 112. There may be more or less layers as well as other components, devices, and elements that are incorporated as part of the discrete sensing device 112. For example, the discrete sensing device 112 can be constructed exclusively of silicon and/or silicon-based materials.

For example, embodiments of the sensing device 100 can have various functions that can be exemplified in one or more of a variety of configurations of the discrete sensing device 112. These configurations can include, but are not limited to, semiconductor-chip based devices, system-on-a-chip based devices, and microelectromechanical system ("MEMS") based devices, among many others. In one example, the discrete sensing device 112 can comprise a piezo-resistive semiconductor die that is responsive to pressure of the working fluid. In another example, the discrete sensing device 112 can comprise a Backside Absolute Pressure ("BAPS") sensor die, and example of which can be provided by General Electric of Fremont, Calif.

Although the shape of the housing 132 is depicted in elongated fashion with curvilinear contours, this shape does not limit the scope and spirit of the present disclosure. The housing 132 in other embodiments of the sensing device 100 can have shapes that define volumes of various configurations. These shapes can be selected based on design preferences, and in one example the shape of the housing 132 is selected because the shape is compatible with the particular application, e.g., the fluid fitting 574 (FIG. 8) below.

A variety of materials are contemplated for use in the housing 132, and by way of a non-limiting listing such materials can include ceramics (e.g., alumina), mullite, glass, semiconductor materials, as well as compositions, combinations, and derivations thereof. In one example, alumina is used to form at least the upper body portion 140 so that the bonding element 124 and/or the discrete sensing device 112 is disposed in contact with the alumina.

Materials and components of the housing 132 can also be selected based on, for example, thermal properties of the material, e.g., the CTE. Exemplary materials that are suited for use as part of the housing 132 can have a CTE of less than about 10 ppm/° C., and one particular construction uses materials in which the CTE is from about 4 ppm/° C. to about 7 ppm/° C. The selection of materials in other examples of the materials for use in the housing 132 can be based, at least in part, on the type of materials used in the construction of and/or the general characteristics of the sensing element 110. This is particularly illustrated in embodiments of the sensing device 100 in which the CTE of materials used in the housing 132 is less than about 300% of the sensing element 110, and/or within about 50% of the bonding element 124.

The materials can likewise be selected to permit the elongated body 134 to be formed monolithically, such as would be found in a single, extruded or molded part. Such materials can also be selected so that the elongated body 134 is formed as elements that can be individually manufactured as, for example, the upper body portion 140 and the lower body portion 138. These separate elements can be assembled together such as by applying a bonding agent (e.g., adhesive), weldment, or by using another suitable technique for securing such parts together. In one example, the technique used to secure the elements together should be compatible with the other features of the sensing device 100, the working fluid, and the CTE of the materials discussed herein.

The bonding element 124 can be solder, solder glass, glass, solder paste, or similarly composed material such as can be useful to attach and secure semiconductor and semiconductor-related device to, e.g., printed circuit boards. Suitable materials for use in bonding element can comprise glass and other silicon-based materials, and in one particular embodiment of the sensing device 100 a glass material is used that can adhere to both alumina and glass (e.g., PYREX). One example of the bonding element 124 such as the glass material can also be compatible with one or more of aluminum, copper, gold, invar, kovar, nickel, stainless steel, tungsten, borosilicate, quartz, silica, soda lime, silicon, gallium arsenide, indium phosphide, silicon carbide, aluminum nitride, boron nitride, sapphire, among others.

The seal 146 can be used to enhance fit, seal together two opposing surfaces, and in at least one example hermetically seal a volume from the surrounding environment such as can be found in implementations in which the elongated body 134 is secured to the fluid fitting 574 (FIG. 8) discussed below. In one embodiment, the seal 146 can be, for example, an o-ring, an annular seal, or other sealing device that extend around at least a portion of, e.g., the elongated body 134 of the housing 132. Although the seal 146 can be constructed of elastomeric, metallic, or composite materials, the exact materials for use as the seals can be selected based on the properties and characteristics of the working fluid, e.g., the temperature and the pressure. Likewise the construction of the seal 146 and the elongated body 134 can be selected separately, and/or in conjunction with one or more of the other components of the fluid fitting discussed below, to optimize the performance of the fit between the elongated body 134 and the corresponding portion of the fluid fitting.

Referring next to FIGS. 4 and 5, another example of a sensing device 200 is shown. The sensing device 200 has features that are also similar to those features discussed in connection with the sensing device 100 above. Therefore, like numerals are used to identify such like features except the numerals are increased by 100 (e.g., 100 is now 200 in FIGS. 4 and 5). For example, in one embodiment the sensing device 200 comprises a sensing region 202, a cavity 204 with a peripheral cavity wall 206, and a discrete sensing device 212 with a primary layer 214 and a supporting layer 216. A bonding element 224 is disposed in the cavity 204, thereby forming a shear or first bonding area 226 and a tensile or second bonding area 228. The sensing device 200 also comprises a substrate 230 in the form of a housing 232 with an elongated housing 234 and a fluid passage 236 and a lower body portion 238 and an upper body portion 240. An indexing feature 242 is provided to prevent or discourage rotation of the sensing device 200. While other features discussed and contemplated in connection with other embodiments (e.g., sensing device 100 (FIGS. 2 and 3) are compatible, positive recitation such similar features is not provided below, however, unless necessary to clarify or explain one or more concepts of the embodiments.

Turning to some of the other features of the sensing device 200, in one embodiment the substrate 230 can comprise an upper housing 248 and a lower housing 250. An inner seal 252 is provided to seal the upper housing 248 and the lower housing 250. The lower housing 250 can have an engagement feature 254 with an outer engagement surface 256 and a restraining element 258, which is configured to secure together the upper housing 248 and the lower housing 250. The restraining element 258 can be formed separately and welded or glued to the lower housing 250, or in another example the restraining element 258 can be formed monolithically with the lower housing 250. The outer engagement surface 256 can form part of the indexing feature 242 (e.g., the tab or flat), and in one embodiment the outer engagement surface 256 can comprise, in addition to or in the alternative to the indexing feature 242, threads and similar fasteners that are configured to engage corresponding features on, e.g., the fluid fitting.

As best illustrated in FIG. 5, in one embodiment the fluid passage 236 can comprise an upper fluid passage 260, which is part of the upper housing 248, and a lower fluid pathway 262 in the lower housing 250. As discussed in more detail in connection with the exemplary implementation below, the combination of the upper fluid passage 260 and the lower fluid passage 262 exposes at least a portion of the discrete sensing device 212 to the working fluid (e.g., fuel, hydraulic fluid, lubricant, or refrigerant). In one example, the bottom surface of the discrete sensing device 212 is responsive to properties of the working fluid.

The lower housing 250 can be configured with a recess 264 and a groove 266. The recess 264 is sized and configured to receive the upper housing 248. This configuration can permit the upper housing 248 to be recessed into the lower housing 250, as illustrated in FIGS. 4 and 5. Recessing can permit overlapping of the restraining element 258 over the periphery of the upper housing 248, thereby preventing the upper housing 248 from being extricated from the lower housing 250. The recess 264 can likewise be sized and configured to engage the inner seal 252 such as to compress, in whole or in part, the inner seal 252 to form an air-tight and/or hermetic seal. Moreover, while shown as being proximate the lower part of the lower body portion 238, the position of the groove 266 can vary in connection with, e.g., implementation of the sensing device 200 in the fluid fitting. The groove 266 can extend annularly around all or a portion of the outer periphery of the lower housing 250. In one example, the dimensions of the groove 266 are compatible with receiving and sealing by way of the seal 246.

In one embodiment, an alignment feature 268 is provided that is useful align the upper housing 248 and the lower housing 250 such as during assembly of the sensing device 200. The alignment feature 268 can include one or more features on each of the upper housing 248 and the lower housing 250 such as, for example, an alignment extension 270 on the upper housing 248 and an alignment interface 272 on the lower housing 250. In one example, the latter, i.e., the alignment interface 272 can be sized and configured to register the alignment extension 270, thereby providing in one construction optimum mating and compression of the inner seal 252.

The upper housing 248 can be generally positioned at the upper body portion 240 so as to expose the upper surface (e.g., the vertical restraining surface 144 (FIGS. 2 and 3). This position likewise exposes the cavity 204, which in the present example is incorporated into the upper housing 248. In one example, the cavity 204 is exposed to permit the bonding element 224 to be received therein, upon which is placed the discrete sensing device 212. The upper housing 248 can be generally constructed of materials compatible with the material of the bonding element 224 (e.g., glass material) discussed above. In one example, the upper housing 248 comprises alumina and/or other materials derivations and compositions of ceramic-based materials.

Figure 6:
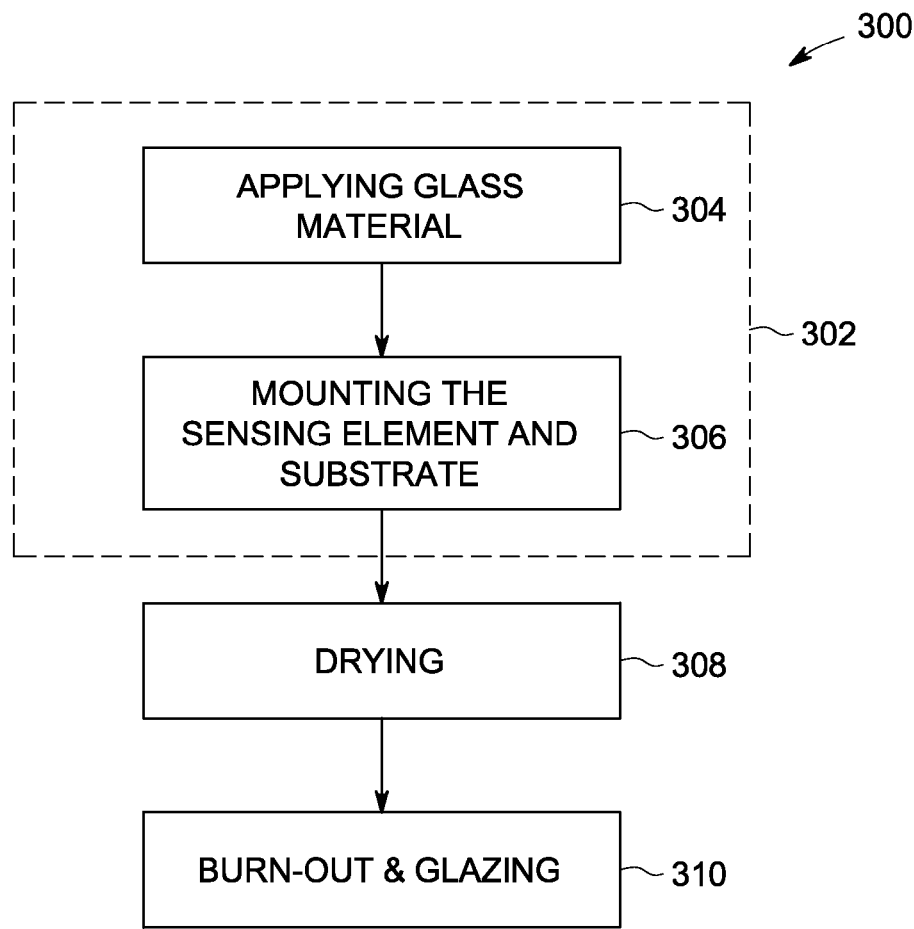
FIG. 6 is a method for assembling a sensing device in still another exemplary embodiment of the invention.

For a more particular example of the processes that can be used to construct a sensing device of the type contemplated herein, reference can now be had to the flow diagram of FIG. 6. It is shown in this diagram a method 300 to attach, for example, the sensing element (e.g., sensing element 22, 110) to the substrate (e.g., substrate 18, 130, 230) using the bonding element (e.g., bonding element 24, 124, 224). In the embodiment of the method 300 shown in FIG. 6 and discussed below, the substrate comprises alumina and the sensing element comprises silicon and PYREX or similar glass substrate, which is mounted onto the alumina using a bonding material compatible with both ceramic and glass and with a CTE of less than 10 ppm/° C. But while this method 300 reflects and is discussed in connection with particular process parameters and materials, it is noted that this method 300 is only one exemplary method and should not limit the scope and content of the present disclosure.

Turning now to steps that are illustrated in the flow diagram of FIG. 6, the method 300 can comprise a plurality of steps 302-310, which in one respect produce at the end of the method 300 one or more functioning sensing devices for use in, for example, the fluid fitting 574 (FIG. 8) discussed below. The method 300 can comprise, at step 302, assembling the sensing device, and in one embodiment of the method 300 the step 302 can comprise at step 304 applying the bonding element (e.g., glass material) to one or more of the substrate and the sensing device, and at step 306 mounting the sensing element (e.g., the discrete sensing device 112, 212) onto the substrate. Each of the step 304 and step 306 can be executed by hand, or by implementing one or more robotic and or automated equipment designed and specified for semiconductor and related printed circuit board assembly.

The method 300 can also comprise, at step 308, drying the assembled sensing device such as by placing the assembled sensing device into an oven, kiln, or by simply applying heat to the assembled sensing device. The method 300 can further comprise, at step 310, burning-out and glazing the assembled sensing device. Processing time and temperature in each of the step 308 and the step 310 can vary, with particular processing controls being established in a manner that provides superior molecular bonding between the sensing element, substrate, and the bonding layer.

Figure 7:
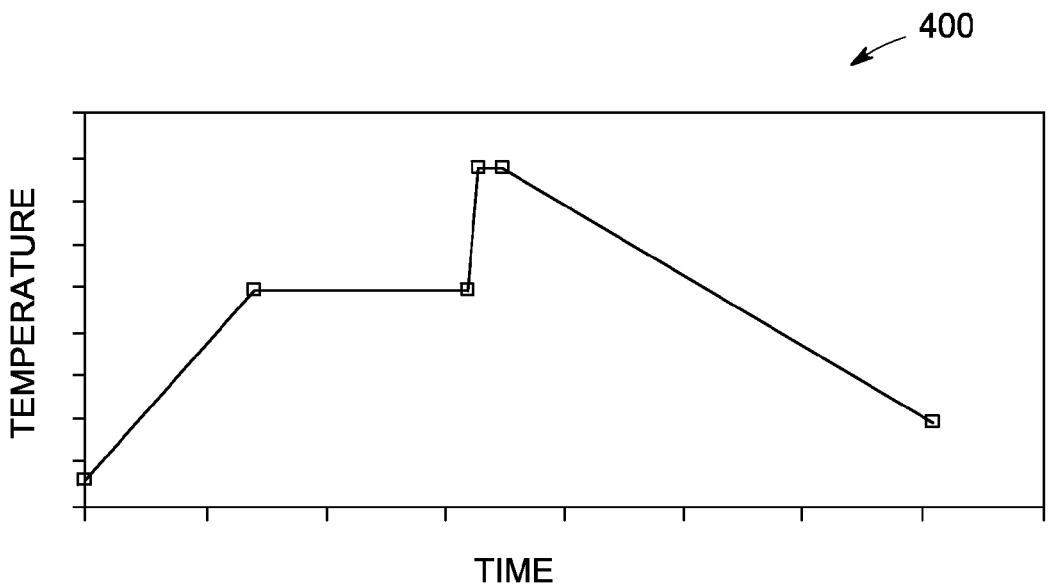
FIG. 7 is a diagram of a temperature profile for use with the method of FIG. 6.

One embodiment of the method 300 can implement a temperature profile 400, such as the temperature profile that is illustrated in FIG. 7. The temperature profile 400 illustrates cycling features of one or more parameters for use in the method 300 above. A combination of temperatures and pressures may be used in the kiln or oven to provide adequate flow to the glass material and elimination of voids within the bonding structure. These parameters can be selected to provide bonds between the sensing element, the substrate, and the bonding layer that eliminate residual stress effects. In one example, the parameters are selected so that a sensing device that results from the method 300 exhibits a minimum burst pressure of at least 3000 psig at 25° C.

When bonded in accordance with embodiments of the method 300, residual stresses can be minimized and the die is effectively secured, or "frozen," relative to the alumina or glass substrate at a temperature substantially above the normal operating temperature of 140° C. In one example, when calibration is performed across the temperature and pressure range of the assembly, the resultant accuracy may be better than 1% of full scale pressure across the temperature range and remains consistent and ultra stable throughout the useful life of the product. The inventors have discovered that this process is unlike epoxy bonding, which will continue to stress relieve itself over time, temperature, pressure and media exposure. Any one of these properties may result in long-term drift in epoxy-bonded materials.

Likewise devices manufactured in accordance with embodiments of the method 300 can be exposed to extreme pressure transients such as transients up to about ten times full-scale pressure without impairing the function of the device. Such devices can also survive temperature transients greater than about 140° C. without impairing function. In one example, burst testing of the device manufactured using embodiments of the method 300 can result in failure above 3000 psig of parent material within the silicon or glass substrate, while retaining the strength of the bonding material.

In view of the forgoing discussion, there is provided below, with reference to FIG. 8, an exemplary implementation of embodiments of sensing devices, such as the sensing devices 10, 100, and 200 discussed in connection with FIGS. 1-7 above. By way of non-limiting example, this implementation comprises a fluid fitting 574, wherein the present example of the fluid fitting 574 has features adapted for fluid-carrying tubing in pressurized environments. Other examples of the fluid fitting 574 can also comprise various other configurations in which one or more of the sensing devices (e.g., sensing devices 10, 100, 200) are utilized to measure and characterize properties of a corresponding working fluid. In one implementation, the fluid fitting 574 can be compatible with harsh, caustic fluids such as fuel, coolant, refrigerant, lubricating oil, or hydraulic fluid of an automobile. In another implementation, a plurality of the sensing devices discussed above can be configured together in a housing, such as a housing of the fluid fitting, in which the dimensions are relatively the same as the dimensions of housings using conventional sensing technology. This configuration of multiple sensing devices of the present disclosure permits different (e.g., pressure measurement and temperature measurement) or multiple (e.g., more than one pressure measurement) sampling of the properties of the working fluid.

The sensing devices can be configured to measure properties such as temperature and pressure of the working fluid, while the fluid fitting 574 can be configured to discharge electrons that can build-up on portions of the fluid fitting 574, such as within the portion of the fluid fitting 574 in which flows the working fluid. These characteristics are beneficial to fluid fittings like fluid fitting 574 because these characteristics permit such fluid fittings to be constructed of materials, e.g., conductive and non-conductive polymers, which can reduce certain parameters such as size, weight, and cost. Likewise these materials can comprise other materials, components, and the like that are useful for protecting fluid fitting (and its associated electrical components) from ESD and ESD-related problems. Additional details of these and other features are discussed in connection with the example of the fluid fitting 574 that is illustrated in FIG. 8 and described below.

Figure 8:
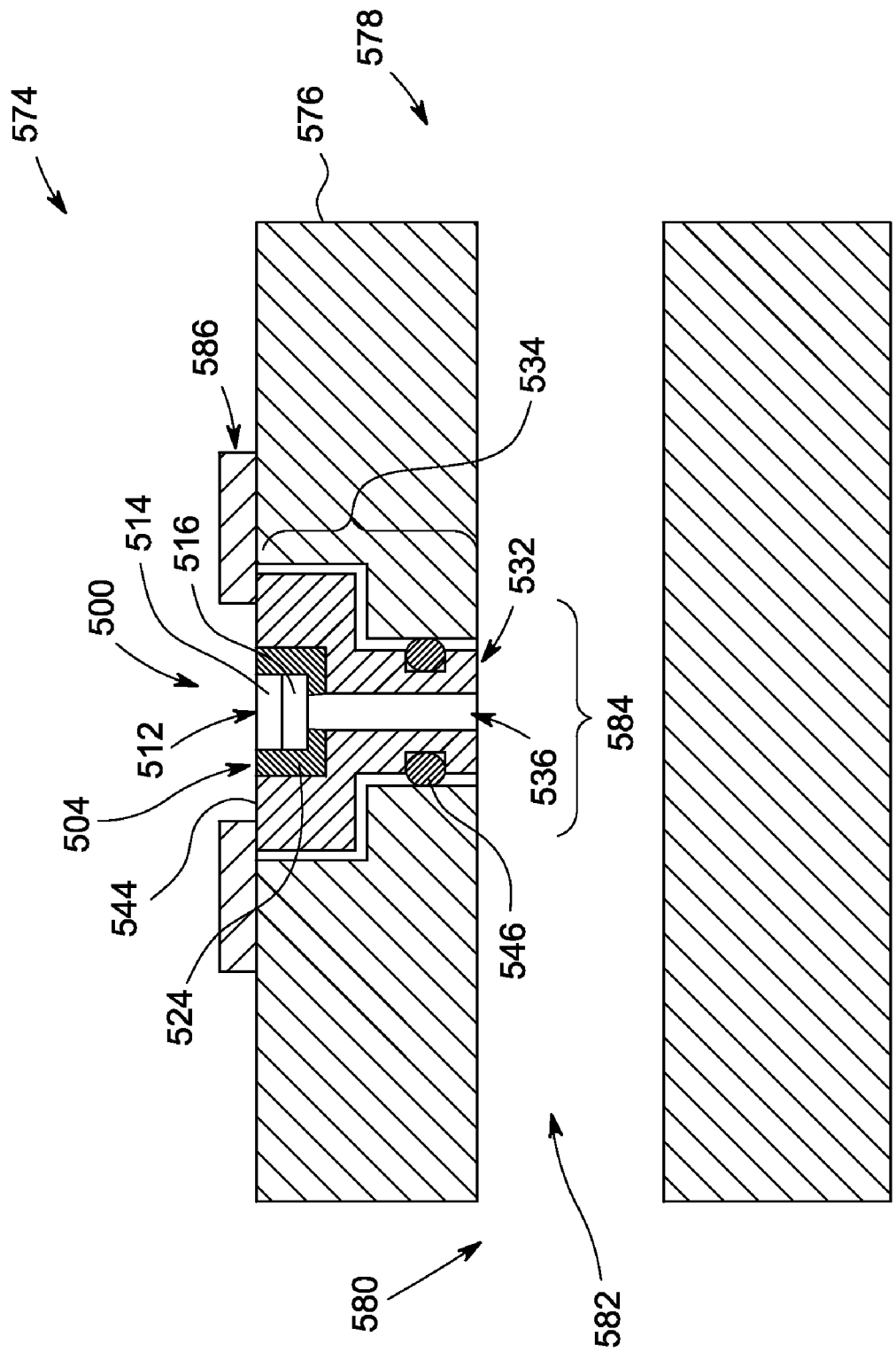
FIG. 8 is a side, cross-section view of a fluid fitting in an exemplary embodiment of the invention.

With reference now to FIG. 8, and by way of non-limiting example, there is shown a sensing device 500 that can comprise a cavity 504 in which is located a discrete sensing device 512 with an primary layer 514 and a supporting layer 516. A bonding element 524 is disposed in the cavity 504 and in surrounding relation to the discrete sensing device 512. The sensing device also comprises a housing 532 that has an elongated body 534 through which extends a fluid passage 536. The housing 532 is formed with a vertical restraining surface 544 and a seal 546, the latter (i.e., the seal 546) being disposed in one example annularly about the housing 532.

The sensing device 500 can be generally incorporated as part of the fluid fitting 574 such as would be found in automotive vehicles, and in one particular application, the fluid fitting 574 can be configured to measure the pressure of fuel in a fuel system. In one example, the fluid fitting 574 can comprise a fitting body 576 with an input side 578, an output side 580, and a fitting pathway 582 that permits a working fluid such as fuel to flow between the input side 578 and the output side 580.

In one embodiment, the fluid fitting 574 comprises an opening 584 that is configured to receive the sensing device 500. The opening 584 can have a shape and features that are complimentary to the sensing device 500. These features can be sized to engage the sensing device 500, such as engagement with the seal 546, so as to seal (e.g., hermetically seal) the fluid fitting 574 for high pressure flow of the working fluid. The fluid fitting 574 can also comprise a restraining device 586, which can engage portions of the sensing device 500 such as the vertical restraining surface 544. This engagement can prevent the sensing device 500 from moving out of the fitting body 576. Examples of the restraining device 586 can be constructed as part of the fitting body 576, as one or more separate pieces attached to the fitting body 576, and also in one example as a device or structure coupled to one or both of the fitting body 576 and the sensing device 500. In one example, threads are also contemplated for use in, e.g., the opening 584. Utilizing these threads in conjunction with complimentary threaded features on the sensing device 500 can secure and engage the sensing device 500 and the fitting body 576.

The sensing device 500 communicates with the fitting pathway 582 via the fluid passage 536. This configuration permits the fluid to interact with the sensing device 500. This interaction can permit data and information about the fluid to be collected, such as, but not limited to, temperature, pressure, flow rate, chemistry, as well other properties consistent with fuel and other fluids of the type disclosed and contemplated herein.

The fitting body 576 of the fluid fitting 574 can be constructed monolithically, such as would be found in a single, extruded plastic part, or as elements that are individually formed and assembled together. In one embodiment, the fitting body 576 can comprise elements that are constructed of different materials, such as one element that can comprise conductive material, and one element that can comprise non-conductive material.

The fitting body 576 and/or each of the elements can be formed of conductive and non-conductive materials, such as conductive and non-conductive polymers, metals (e.g., stainless steel), as well as composites and any combinations thereof. The elements can be coated with materials that can be selected because of their compatibility with the fluid, and the fluid medium, such as is the case with materials that have physical and/or chemical properties that resist corrosion in caustic environments. Manufacturing processes implemented to make the elements of the fluid fitting 574 include casting, molding, extruding, machining (e.g., turning, and milling) and other techniques are suitable for forming the various elements and components of the fluid fitting 574, some of which are disclosed and described herein. Because these processes, and the materials that are utilized by such processes, are generally well-known to those having ordinary skill in the automotive arts, no additional details will be provided herein, unless such details are necessary to explain the embodiments and concepts of the fluid fittings contemplated herein.

When the construction of the fitting body 576 comprises multiple elements, it is further contemplated that the fitting body 576 can comprise connective features that are used to couple the various elements together. These can include mechanical fasteners such as screws, adhesives, welds, and the like. These connective features can be selected so that they are likewise compatible with the particular application, such as by selecting materials for adhesives and weldments that are compatible with high temperatures (e.g., in excess of about 140 C.), and high pressures (e.g., in excess of about 500 psi), which may be found in the automotive vehicle.

Each of the input side 572 and the output side 574 can be configured to couple tubing such as fuel lines with the fitting body 576. This coupling can include the use of mechanical interfaces such as threaded fasteners, hose clamps, barbed and similarly shaped devices. Each of these interfaces can engage a portion of the fuel line to secure the fuel line to the fitting, and permit fuel to travel from the fuel line and into the fitting pathway 582 of the fluid fitting 574. The interfaces are likewise operatively configured to retain pressure within the various lines, as well as to maintain the overall properties of the fuel such as pressure and/or temperature that is required by automotive vehicles.

As discussed above, sensor devices of the type used as the sensing device 500 can be configured to sense a variety of properties including, but not limited to, temperature, pressure, fluid flow properties (e.g., flow rate), fluid chemical properties (e.g., viscosity, conductivity, levels of contaminants, and chemical composition), among many others. These sensors can collect data, which can then be processed, transferred from the fluid fitting 574, or otherwise manipulated for purposes of, e.g., optimizing systems and performance of the automotive vehicle.

Examples of the fluid fitting 574 can also comprise one or more groups of electrical circuits that are each configured to operate, separately or in conjunction with other electrical circuits, to monitor the properties of the fluid, such as the properties described herein. The electrical circuits that are used to implement the embodiments of the sensing devices can be constructed in a manner that interconnect a variety of electrical elements that comprise, but not limited to, resistors, capacitors, transistors, transmission lines, and switches. They may further communicate with other circuits (and/or devices), which execute high-level logic functions, algorithms, as well as process firmware, and software instructions. Exemplary circuits of this type include, but are not limited to, field programmable gate arrays ("FPGAs"), and application specific integrated circuits ("ASICs"). While all of these elements, circuits, and devices function individually in a manner that is generally understood by those artisans that have ordinary skill in the electrical arts, it is their combination and integration into functional groups and circuits that generally provide for some embodiments of the sensing devices that are disclosed and described herein.

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A sensing device comprising:
    a sensing region;
    a sensing element disposed in the sensing region; and
    a bonding element,
        wherein the bonding element forms a first bonding area that comprises a molecular bond between the bonding element and a side of the sensing element, and
        wherein the bonding element has a coefficient of thermal expansion that is less than about 10 ppm/° C.

2. A sensing device according to claim 1, wherein the bonding element covers at least about 50 of the side of the sensing element.

3. A sensing device according to claim 1, wherein the bonding element comprises silicon-based materials.

4. A sensing device according to claim 1, wherein the bonding element forms molecular bonds with alumina and glass.

5. A sensing device according to claim 1, further comprising a receptacle in the sensing region, wherein the sensing element is located in the receptacle.

6. A sensing device according to claim 5, wherein the receptacle comprises a wall in surrounding relation to the sensing element, and wherein the bonding element forms a molecular bond between the bonding element and the wall.

7. A sensing device according to claim 1, further comprising a second bonding area forming a molecular bond with a bottom of the sensing element.

8. A sensing device according to claim 1, further comprising:
    an elongated cylindrical body; and
    a seal disposed annularly about the elongated cylindrical body,
        wherein the sensing region is integrated into the elongated cylindrical body.

9. A sensing device according to claim 1 wherein the sensing element comprises a piezo-resistive semiconductor die that is responsive to pressure of the working fluid.

10. A sensing device according to claim 1 wherein the sensing element comprises a microelectromechanical system (MEMS) device.

11. A device for measuring a property of a working fluid, said device comprising:
    a substrate with a cavity having a peripheral wall;
    a discrete sensing device having a bonded portion disposed in the cavity; and
    a bonding element disposed between the bonded portion and the peripheral wall, the bonding element forming a molecular bond with the bonded portion and the peripheral wall,
        wherein the bonding element has a coefficient of thermal expansion that is less than about 10 ppm/° C.

12. A device according to claim 11, wherein the bonding element comprises glass.

13. A device according to claim 11, wherein the discrete sending device is configured to measure pressure.

14. A device according to claim 11, wherein the cavity has a bottom wall, and wherein the bonding element forms a molecular bond with the bottom wall.

15. A device according to claim 11, wherein the bonded portion comprises at least 50% of a side of the discrete sensing device.

16. A device according to claim 15, wherein the bonded portion comprises at least about 30% of the total exterior surface area of the discrete sensing device.

17. A device according to claim 11, wherein the substrate forms an elongated cylindrical body.

18. A device according to claim 17, further comprising a seal dispose annularly on the elongated cylindrical body.

19. A device according to claim 11, wherein the substrate comprises one or more of alumina, glass, ceramics, and combinations and derivations thereof.

20. A device according to claim 11, wherein the peripheral wall is formed integrally with the substrate.

* * * * *

UNITED STATES PATENT AND TRADEMARK OFFICE
CERTIFICATE OF CORRECTION

| | |
|---|---|
| PATENT NO. | : 8,261,618 B2 |
| APPLICATION NO. | : 12/951330 |
| DATED | : September 11, 2012 |
| INVENTOR(S) | : Engle et al. |

It is certified that error appears in the above-identified patent and that said Letters Patent is hereby corrected as shown below:

In Column 13, Line 19, in Claim 2, delete "50" and insert -- 50% --, therefor.

Signed and Sealed this
Twenty-second Day of January, 2013

David J. Kappos
*Director of the United States Patent and Trademark Office*